(12) United States Patent
Tanahashi et al.

(10) Patent No.: US 9,662,233 B2
(45) Date of Patent: May 30, 2017

(54) ANTITHROMBOTIC ARTIFICIAL BLOOD VESSEL

(71) Applicant: Toray Industries, Inc., Tokyo (JP)

(72) Inventors: Kazuhiro Tanahashi, Otsu (JP); Yuka Sakaguchi, Otsu (JP); Masaki Fujita, Otsu (JP); Koji Kadowaki, Otsu (JP); Hiroshi Tsuchikura, Otsu (JP); Satoshi Yamada, Otsu (JP)

(73) Assignee: Toray Industries, Inc. (JP)

( * ) Notice: Subject to any disclaimer, the term of this patent is extended or adjusted under 35 U.S.C. 154(b) by 73 days.

(21) Appl. No.: 14/783,907

(22) PCT Filed: Apr. 10, 2014

(86) PCT No.: PCT/JP2014/060378
§ 371 (c)(1),
(2) Date: Oct. 12, 2015

(87) PCT Pub. No.: WO2014/168198
PCT Pub. Date: Oct. 16, 2014

(65) Prior Publication Data
US 2016/0067065 A1     Mar. 10, 2016

(30) Foreign Application Priority Data

Apr. 12, 2013   (JP) .................................. 2013-084122

(51) Int. Cl.
*A61F 2/06* (2013.01)
*A61F 2/86* (2013.01)
(Continued)

(52) U.S. Cl.
CPC .................. *A61F 2/86* (2013.01); *A61F 2/06* (2013.01); *A61L 27/18* (2013.01); *A61L 27/507* (2013.01);
(Continued)

(58) Field of Classification Search
CPC ................ A61F 2/06; A61F 2210/0076; A61F 2230/0069; A61F 2250/0067; A61F 2310/00389
See application file for complete search history.

(56) References Cited

U.S. PATENT DOCUMENTS

| | | | |
|---|---|---|---|
| 4,695,280 A | 9/1987 | Watanabe et al. | |
| 5,322,659 A * | 6/1994 | Walder | A61L 27/54 264/171.26 |

(Continued)

FOREIGN PATENT DOCUMENTS

| | | |
|---|---|---|
| JP | 54-83095 A | 7/1979 |
| JP | 59-225052 A | 12/1984 |

(Continued)

OTHER PUBLICATIONS

Y. Okuda, et al., "Immobilization and release-control of heparin on the ePTFE vascular grafts", The Annual Meeting of the Japanese Society for Biomaterials Yokoshu, 1995, vol. 17, p. 33, 1-I-5 w/English translation, (Oct. 1995).

*Primary Examiner* — Paul Prebilic
(74) *Attorney, Agent, or Firm* — DLA Piper LLP (US)

(57) ABSTRACT

An artificial blood vessel is a tubular fabric including a fiber layer containing an ultrafine fiber(s) and an ultrafine fiber layer in the inside of the fiber layer, the ultrafine fiber layer being composed of an ultrafine fiber(s) having a fiber diameter(s) of not less than 10 nm and not more than 3 μm, wherein a quaternary ammonium group-containing polymer having alkyl groups each of a carbon number 10 or less is covalently bound to the ultrafine fiber(s); heparin is ionically bound to the quaternary ammonium group-containing polymer; and the residual heparin activity after washing with physiological saline at 37° C. for 30 minutes is 20 mIU/cm2 or more.

15 Claims, 1 Drawing Sheet

(51) Int. Cl.
*A61L 27/50* (2006.01)
*A61L 27/54* (2006.01)
*A61L 27/18* (2006.01)
*A61L 33/00* (2006.01)

(52) U.S. Cl.
CPC ........... *A61L 27/54* (2013.01); *A61L 33/0023* (2013.01); *A61F 2310/00389* (2013.01); *A61L 2300/42* (2013.01)

(56) References Cited

U.S. PATENT DOCUMENTS

| | | | |
|---|---|---|---|
| 5,986,168 | A | 11/1999 | Noishiki |
| 6,053,939 | A | 4/2000 | Okuda et al. |
| 2004/0213818 | A1 | 10/2004 | Kashiwabara et al. |
| 2015/0352265 | A1* | 12/2015 | Garimella ........... A61L 33/0076 424/423 |

FOREIGN PATENT DOCUMENTS

| | | | |
|---|---|---|---|
| JP | 63-115554 | A | 5/1988 |
| JP | 63-115555 | A | 5/1988 |
| JP | 8-336587 | A | 12/1996 |
| JP | 9-276394 | A | 10/1997 |
| JP | 3341503 | B | 11/2002 |
| JP | 3799626 | B | 7/2006 |
| JP | 4273965 | B | 6/2009 |
| JP | 4627978 | B | 2/2011 |
| WO | 00/13719 | A1 | 3/2000 |

* cited by examiner

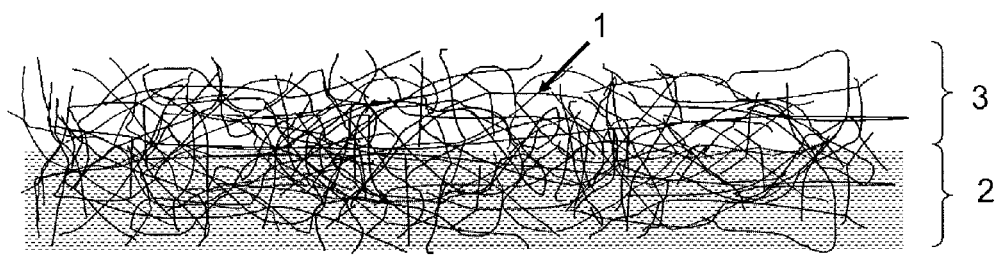

ANTITHROMBOTIC ARTIFICIAL BLOOD VESSEL

TECHNICAL FIELD

This disclosure relates to an artificial blood vessel to be used for reconstruction, repair, or replacement of a blood vessel that has undergone damage and/or the like.

BACKGROUND

The number of patients suffering from arteriosclerosis is increasing due to population aging and an increase in the population with metabolic syndrome. Arteriosclerosis is an abnormality of arterial walls. In arteriosclerosis, a hyperglycemic state or hyperlipidemic state of blood causes degeneration of the vascular wall and, as a result, the vascular wall becomes weak or thickened, or calcification occurs to make the vascular wall hard and fragile. Although such blood vessel degeneration may occur at any site in the blood vessels in the body, peripheral blood vessels are especially remarkably affected by the degeneration.

Treatment of such a degenerated blood vessel is conventionally carried out by a minimally invasive endovascular treatment such as balloon dilation or stent placement using a catheter, or by surgery for replacement of the damaged blood vessel with a blood vessel of the patient him or herself or with an artificial blood vessel.

However, when an artificial blood vessel is used, the body recognizes the artificial blood vessel as a foreign substance, and blood clotting reaction proceeds on the blood-contacting surface of the artificial blood vessel to form a thrombus. A blood vessel in the body has an intima having vascular endothelial cells on its surface contacting with blood, and the intima plays a role in inhibiting formation of a thrombus. Also, in an indwelling artificial blood vessel, vascular endothelial cells cover the blood-contacting surface of the artificial blood vessel to form an intima. However, since the artificial blood vessel is recognized as a foreign substance until the intima is covered with the endothelial cells, means for preventing thrombus formation is required until formation of the intima. In particular, at a site where an artificial blood vessel having a small diameter is used, the blood flow is low so that deposition of thrombi easily occurs, and the blood vessel is likely to be clogged even with a small amount of thrombi. At present, the long-term performance of artificial blood vessels having small diameters is not good, and none of such artificial blood vessels is applicable for clinical use.

To solve these problems, development of artificial blood vessels has been conventionally carried out focusing on early intimal formation and early establishment of antithrombogenicity.

Examples of methods of promoting intimal formation include a method in which a growth factor or an inducer of cells is carried by the artificial blood vessel, and a method in which an artificial blood vessel containing, as its constitutional material, a fabric, knit, or non-woven fabric of a fiber such as a polyester fiber is used. In particular, it is known that, when an ultrafine fiber of less than 10 μm is included, the size of the ultrafine fiber or the size of the fiber gap is suitable for cell growth or cell infiltration (JP 1875991 B, JP 1870688 B and JP 1338011 B). It is also known that ultrafine fibers have effects to promote adhesion of platelets and prevent leakage of blood from the blood vessel wall when the fibers are indwelling (JP 4627978 B).

In a conventional method of imparting antithrombogenicity to an artificial blood vessel, heparin is carried by the artificial blood vessel. Since the fiber itself does not have a capacity to carry heparin, as methods of making the artificial blood vessel to carry a sufficient amount of heparin, a method in which a gel composed of a biodegradable polymer or gelatin containing heparin is filled into the gaps among the fibers (JP 3799626 B), and a method in which heparin is immobilized on the fiber surface by covalent bonds (Japanese Translated PCT Patent Application Laid-open No. 2009-545333) are known.

In addition, since heparin is ionically negatively charged, a method of carrying heparin on a surface of a base of a medical device by forming an ionic bond to a positively charged substance is known. By placing such a base in a body fluid or an aqueous solution, heparin is released over time. Since the antithrombogenicity can be controlled by controlling the release rate, combinations with various positively charged substances have been studied. A method in which an ion complex is formed with a quaternary ammonium compound and the ion complex is coated on a surface (JP 4273965 B); a method in which a polymer containing tertiary amino groups is coated, the tertiary amino groups are converted to quaternary ammonium groups, and heparin is bound thereto by ionic bonds (JP 3341503 B); and a method in which heparin is ionically bound to a surface of a base to which polyethyleneimine which is a polycation is bound (WO 00/13719 and JP 08-336587 A) are known.

However, when fiber gaps are filled such as in the artificial blood vessel described in JP 3799626 B, cellular infiltration is prevented to cause a delay in intimal formation and, furthermore, platelets adhere to gelatin and the like to rather promote thrombus formation, which is problematic. When heparin is immobilized on the fiber surface by covalent bonds such as in the artificial blood vessel described in Japanese Translated PCT Patent Application Laid-open No. 2009-545333, the amount of heparin that can be bound to the surface is limited because of the large molecular weight of heparin, and there is no long-term effect, which is problematic.

With the method described in JP 4273965 B in which an ion complex is formed with a quaternary ammonium low molecular compound, and the ion complex is dissolved in an organic solvent and coated on a surface of a base, a solvent which can dissolve the ion complex and which does not dissolve the base to be coated must be selected so that the solvent is limited. In addition, there is a problem in that since the hydrophilic moiety in the ion complex avoids the organic solvent to mutually coagulate during the coating solution is evaporated to cause a phase separation, the solution cannot be uniformly coated so that the release of heparin cannot be controlled. Further, since the quaternary ammonium low molecular compound and the surface of the base are not bound, the quaternary ammonium itself is also peeled off from the base, which is also a reason why the release of heparin cannot be controlled. With the method described in JP 3341503 B in which a polymer containing tertiary amino groups is coated, the amino groups are converted to quaternary ammonium, and heparin is bound ionically, a thick coating is required to carry a requisite amount of heparin. Therefore, when the polymer is coated on a base requiring a fine structure, the fine structure is buried so that the compatibility with cells is largely degraded. Further, since there is no bond with the surface of the base, when it is desired to firmly adhere the polymer, a solvent which also dissolves the base together with the polymer should be selected so that the solvent is limited. The solvent which dissolves the base used in artificial vessels such as polyester and polytetrafluoroethylene is very few. If the treatment described in JP 3341503 B is performed using a usual solvent, the polymer is readily peeled off, which is problematic with respect to safety when applied to humans.

Further, with the method described in WO 00/13719 and JP 08-336587 A in which heparin is ionically bound to a surface of a base to which polyethyleneimine which is a polycation is bound, since the primary to tertiary amino groups contained in the polyethyleneimine are weakly basic, part of the amino groups are not positively charged in an aqueous solution in which the heparin is ionically bound. As a result, the ionic interaction with heparin is weak so that the amount of the heparin which can be carried is limited.

Thus, even if the known technologies are used, conventional artificial blood vessels have failed in simultaneous achievement of cellular affinity and antithrombogenicity and, in particular, there is no artificial blood vessel having a small diameter that is available for long-term clinical use at present in the world.

In view of this, it could be helpful to provide an artificial blood vessel which promotes intimal formation after indwelling, and is capable of maintaining antithrombogenicity during intimal formation and maintaining its patency for a long time.

SUMMARY

We discovered that, by binding a quaternary ammonium group-containing polymer to ultrafine fiber(s) and, further, by binding ionically heparin to the quaternary ammonium group-containing polymer, antithrombogenicity can be imparted while the fine structure composed of the ultrafine fiber(s) is maintained, that is, both cellular affinity and antithrombogenicity can be realized.

We thus provide the following (1) to (8).

(1) An artificial blood vessel which is a tubular fabric comprising a fiber layer containing an ultrafine fiber(s) and an ultrafine fiber layer in the inside of the fiber layer, the ultrafine fiber layer being composed of an ultrafine fiber(s) having a fiber diameter(s) of not less than 10 nm and not more than 3 μm, wherein a quaternary ammonium group-containing polymer having alkyl groups each of a carbon number 10 or less is covalently bound to the ultrafine fiber(s); heparin is ionically bound to the quaternary ammonium group-containing polymer; and the residual heparin activity after washing with physiological saline at 37° C. for 30 minutes is 20 mIU/cm$^2$ or more.

(2) The artificial blood vessel according to (1), wherein the amount of cation bound to the surface of the fiber(s) is 1 μg/cm$^2$ or more.

(3) The artificial blood vessel according to (1) or (2), whose water permeability at 120 mmHg is not less than 100 mL/cm$^2$/min and less than 4000 mL/cm$^2$/min.

(4) The artificial blood vessel according to any one of (1) to (3), wherein the fiber layer is composed of the ultrafine fiber(s) and a multifilament(s) having a total fineness of 1 to 60 decitex.

(5) The artificial blood vessel according to (4), wherein the fineness of single yarns constituting the multifilament is 0.5 to 10.0 decitex.

(6) The artificial blood vessel according to any one of (1) to (5), having a platelet adhesion rate of less than 20%.

(7) The artificial blood vessel according to any one of (1) to (6), wherein the tubular fabric is composed of a polyester fiber(s).

(8) The artificial blood vessel according to any one of (1) to (7), wherein the inner diameter of the tubular fabric is not less than 1 mm and less than 10 mm.

An artificial blood vessel which promotes intimal formation after indwelling, and is capable of maintaining antithrombogenicity during the intimal formation, and maintaining its patency for a long time can be provided.

BRIEF DESCRIPTION OF THE DRAWING

FIG. 1 is a schematic diagram showing the fiber structure of the artificial blood vessel.

DESCRIPTION OF SYMBOLS

1 . . . Ultrafine fiber, 2 . . . Fiber layer, 3 . . . Ultrafine fiber layer

DETAILED DESCRIPTION

The ultrafine fiber means a fiber having a fiber diameter of not less than 10 nm and not more than 3 μm. When an artificial blood vessel having an ultrafine fiber is used, the number of scaffolds suitable for adhesion of living cells remarkably increases because of the extreme fineness of the fiber, and excellent cellular infiltration can be achieved. Favorable intimal formation occurs in an extremely early phase, and leakage of blood hardly occurs.

Since a strength that allows the artificial blood vessel to follow blood pressure and movement of tissues cannot be exerted with only ultrafine fibers, the artificial blood vessel has a fiber structure composed of, as shown in FIG. 1, a fiber layer 2 in which ultrafine fibers 1 are dispersed in gaps of a basic tissue formed by a coarse texture, stitch or the like constituted of thick fibers; and an ultrafine fiber layer 3 composed of ultrafine fibers 1 inside the fiber layer 2. The artificial blood vessel is formed by making this fiber structure into a tubular shape.

As a production method of forming the fiber structure in which ultrafine fibers are dispersed in gaps of a basic tissue formed by a coarse texture, stitch or the like, a common production method for ultrafine fibers may be employed. Together with a fiber having a size suitable for the strength of the basic tissue, a multicomponent fiber having a sea-island structure is subjected to weaving, knitting, or processing into a braid or a non-woven fabric, and then the sea structure of part of the multicomponent fiber is dissolved using an alkali or the like to perform ultrafining treatment. By this, the ultrafine fiber in the base fabric and the ultrafine fiber layer are preferably prepared.

Thereafter, a gap structure which is more desirable for cells can be achieved by interlacing the ultrafine fiber with the basic tissue by a water-jet process, air-jet process or the like. To allow more effective exertion of the cellular affinity, formation of the ultrafine fiber layer on the blood-contacting surface can be further promoted by a method in which, for example, the blood-contacting surface is rubbed with a file to fuzz the surface.

The fiber material is not limited as long as it is a polymer having biocompatibility. Examples of the fiber material include polyester, polyethylene, polytetrafluoroethylene, polyurethane, polyamide, and nylon. Among these fiber materials, polyester, especially polyethylene terephthalate, is preferred since it has been conventionally clinically used as a material of artificial blood vessels, and has excellent strength.

The fiber may be in any form, and examples of the form include a spun yarn, multifilament yarn, monofilament yarn, and film split fiber yarn. From the viewpoint of strength, uniformity of physical properties, and flexibility, a multifilament yarn is excellent as the form of the fiber. The yarn may be either untwisted or twisted. The yarn may be crimped to a certain extent.

The total fineness of the fiber is preferably 1 to 60 decitex (Dtex), more preferably 1 to 40 decitex. The lower limit of the total fineness is more preferably 5 decitex, most preferably 10 decitex. The upper limit of the total fineness is more preferably 35 decitex, most preferably 25 decitex. With a total fineness of not less than 1 decitex, the strength required for the basic structure of the artificial vessel can be maintained and, with a total fineness of not more than 40 decitex, the thickness of the basic structure of the artificial vessel can be reduced.

The single yarn fineness is preferably 0.5 to 10 decitex (Dtex), more preferably 0.5 to 3.0 decitex. The lower limit of the single yarn fineness is more preferably 1 decitex, and the upper limit of the single yarn fineness is more preferably 2 decitex. When the single yarn fineness is not less than 3 decitex, the flexibility is deteriorated. When the single yarn fineness is not more than 0.5 decitex, the hydrolysis rate is high and there is a problem of deterioration of the strength.

In the tubular fabric which forms the artificial blood vessel, the cloth is provided as a fabric because of its excellent dimensional stability and strength.

To increase the amount of the quaternary ammonium group-containing polymer immobilized on the fiber surface, ultrafine single-yarn-fineness multifilament yarns may be effectively placed in a part of the cloth. The single-yarn fiber diameter of this ultrafine single-yarn-fineness multifilament yarns is preferably 10 nm to 20 μm, more preferably 10 nm to 3 μm, most preferably 0.8 to 1.2 μm.

The size and the amount of the fiber gaps in the fiber layer and the ultrafine fiber layer of the artificial blood vessel can be represented using as an index the water permeability under a pressure of 120 mmHg, and the fiber gap is preferably 100 mL/cm$^2$/min. to 4000 mL/cm$^2$/min. To form an intima containing a stable vascular endothelial cell layer on the blood-contacting surface of the artificial blood vessel, a cell layer which supports the intima and mainly contains vascular smooth muscle and fibroblasts is important. Cells in this cell layer, together with vascular endothelial cells that migrate on the surface of the blood vessel, pass through fiber gaps and infiltrate from the anastomotic site into the inside. Vascular endothelial cells not only infiltrate from the anastomotic site, but also infiltrate from sites on the inner wall of the artificial blood vessel where openings are formed by blood capillaries that infiltrated from the outer wall of the artificial blood vessel through fiber gaps.

In view of this, the fiber gap is preferably not less than 100 mL/cm$^2$/min since, in such cases, intimal formation due to infiltration of the inside of the fiber layer by cells and blood capillaries easily occurs. When the fiber gap is not more than 4000 mL/cm$^2$/min., cellular pseudopodia more easily reach the inside of the fiber layer, and fill the gaps to prevent blood leakage, which is preferred.

The size of the artificial blood vessel is not limited. The artificial blood vessel is most effective as a thin artificial blood vessel having an inner diameter of not less than 1 mm and less than 10 mm.

The artificial blood vessel realizes both cellular affinity and antithrombogenicity by binding a quaternary ammonium group-containing polymer having three alkyl groups each of a carbon number 10 or less to the surface of the fibers and ultrafine fibers constituting the basic tissue and further binding heparin to the quaternary ammonium group-containing polymer by ionic bonding.

Heparin is not particularly restricted as long as it can inhibit the blood coagulation reaction, and examples of heparin include the heparin generally and widely used clinically, unfractionated heparin and low molecular heparin, as well as the heparin having a high affinity to antithrombin III.

Since heparin is a large molecule having a molecular weight of 30,000 to 35,000 Daltons, it can be immobilized on the surface in only a limited amount. Although low-molecular-weight heparins, whose molecular weights are lower than that of heparin, are also clinically used, even these low-molecular-weight heparins have molecular weights of as large as 4,000 to 6,000, which are about 10 times the molecular weights of synthetic antithrombin substances. Heparin can inhibit the activity of thrombin only after binding to antithrombin III and thrombin. Since the binding sites of antithrombin III and thrombin are separately present in the molecule, it is very difficult to control immobilization on the surface while allowing these binding sites to be arranged in optimum positions. This difficulty also causes the low reaction efficiency of immobilization on the surface. Therefore, the quaternary ammonium group-containing polymer is bound to the surface of the fibers and heparin is ionically bound to the quaternary ammonium group-containing polymer.

More specifically, a method in which a polymer containing amino groups such as polyethyleneimine, polyallylamine or polylysine which are polycations is immobilized on the surface and the amino groups are then converted to quaternary ammonium; a method in which a polymerizable monomer containing an amino group is graft-polymerized to the surface, and the amino groups are then converted to quaternary ammonium; or a method in which a quaternary ammonium group-containing polymer such as polydiallyldimethylammonium chloride is immobilized on the surface of the fibers is selected.

The method of immobilizing the polymer containing amino groups or quaternary ammonium groups is not particularly limited, and a method other than a method in which a polymer solution is coated on the surface of the fibers and then evaporating the solvent is selected. A method in which reactive functional groups are introduced to the surface of the fibers and then the polymer is bound by chemical reaction; a method in which the fibers are irradiated with a high-energy beam such as γ-ray or electron beam under the conditions wherein the fibers are immersed in an aqueous solution of the polymer containing amino groups or quaternary ammonium groups, or a method in which the fibers are subjected to plasma treatment and then the fibers are made to contact a solution of a polymer containing amino groups or quaternary ammonium, is preferably employed.

The molecular weight and the chemical structure of the polymer are not restricted, and a low molecular polymer having a molecular weight of 1000 to 50,000, or even when the polymer has a large molecular weight of more than 50,000, a polymer having a branched structure is preferred.

As the method of converting the amino groups in the amino group-containing polymer immobilized on the surface of the fibers to quaternary ammonium groups, a method in which a reaction is carried out in a solution dissolving a haloalkyl compound such as an alkyl bromide is most preferred.

If the carbon number of the alkyl groups contained in the quaternary ammonium group-containing polymer is too many, hydrophobicity is increased and heparin cannot bind to the cationic groups. Therefore, the carbon number per one alkyl group is preferably 10 or less and, in view of the affinity to heparin and ease of handling during the reaction for conversion to quaternary ammonium groups, the carbon number is most preferably 2 to 6. It is not necessary that the three alkyl groups constituting the quaternary ammonium have the same carbon number, but the carbon number of the alkyl groups may be different.

As the method of binding heparin to the fibers whose surface has quaternary ammonium groups, a method in which the fibers are immersed in an aqueous heparin solution is most preferred. The temperature of the aqueous solution, time and pH may be appropriately selected.

The antithrombogenicity and the cellular affinity of the artificial blood vessel are shown by measurement of water permeability, residual heparin activity on the fiber surface after washing, amount of cations on the fiber surface, platelet adhesion rate, cell adhesion rate, and thrombus adhesion.

Water Permeability

Two sites are randomly sampled from the artificial blood vessel, and measurement is carried out twice for each sample by the method described below, followed by calculating the arithmetic mean of the measured values. The artificial blood vessel was cut along the axial direction, and a sample piece having a size of 1 cm×1 cm is prepared. Between two doughnut-shaped packings with a diameter of 4 cm on each of which a hole having a diameter of 0.5 cm is formed by punching, the fabric sample having a size of 1 cm×1 cm is sandwiched such that liquid flow is allowed only through the punched portion. The resultant is stored in a housing for a circular filtration filter. Water filtered through a reverse osmosis membrane is passed through this circular filtration filter at a temperature of 25° C. for not less than 2 minutes until the sample piece sufficiently contains water. Under the conditions of a temperature of 25° C. and a filtration differential pressure of 120 mmHg, external-pressure dead-end filtration of water filtered through a reverse osmosis membrane is carried out for 30 seconds to measure the amount of the water (mL) that permeates the portion with a diameter of 1 cm. The permeation volume is calculated by rounding the measured value to an integer. By converting the permeation volume (mL) to the value per unit time (min.) per effective area on the sample piece ($cm^2$), the water permeability at a pressure of 120 mmHg is determined.

About the artificial vessel after the immobilization of heparin, the binding ability of the heparin bound to the fiber surface can be measured by the method of measuring the residual heparin activity on the fiber surface described below. As for the residual heparin activity on the fiber surface, the higher the better the residual heparin activity, and the the residual heparin activity is preferably 20 mIU/$cm^2$ or more.

Method of Measuring Residual Heparin Activity on Fiber Surface

An artificial vessel is cut open in the axial direction and a sample piece sizing 1 cm×1 cm is cut out. The piece is washed with 10 mL of physiological saline at 37° C. for 30 minutes. The washed sample is subjected to the reaction according to the instructions of Testteam Heparin S (Sekisui Medical Co., Ltd.), and the absorbance at 405 nm is measured using a microplate reader (Corona Electric Co., Ltd., MTP-300), and the heparin activity is calculated in accordance with the instructions of the kit.

With respect to the artificial vessel after the immobilization of heparin, the amount of the cation bound to the fiber surface can be measured by the method of measuring the amount of cation on the fiber surface described below. As for the amount of the cation on the fiber surface, the larger the amount of the cation, the better, and the amount of the cation is preferably 1 μg/$cm^2$ or more.

Method of Measuring Amount of Cation on Fiber Surface

One gram of a ring-shaped sample prepared by cutting the artificial blood vessel into round slices in the transverse direction is cut into 10 small pieces each having a weight of 0.1 g along the longitudinal direction of the original blood vessel, and extraction is performed with 10 mL of physiological saline per 1 g of sample at 37° C. for 24 hours. The sample after the extraction is stained with Orange II (molecular weight: 350.33, Wako Pure Chemical Industries, Ltd.) solution in acetate buffer (pH 4.0) at 37° C. for 1 hour, and the sample is then washed with the same buffer and water, respectively, for 10 minutes each. The sample is treated with 1 mM aqueous sodium hydroxide solution at 37° C. for 30 minutes to extract Orange II, and the extract is neutralized with 21 mM hydrochloric acid. The absorbance at 482 nm and 550 nm is measured using a microplate reader (Corona Electric Co., Ltd., MTP-300), and the absorbance at 550 nm is subtracted from the absorbance at 480 nm. Using a calibration curve separately prepared, the bound cation is quantified from the absorbance.

In the artificial blood vessel after immobilization of the antithrombin active agent, the platelet adhesion rate on the fiber surface can be measured by the following method of measuring the platelet adhesion rate on the fiber surface. The lower the platelet adhesion rate on the fiber surface, the better. The platelet adhesion rate on the fiber surface is preferably less than 20%.

Method of Measuring Platelet Adhesion Rate on Fiber Surface

The artificial blood vessel is cut along the axial direction and a disk sample with a diameter of 12 mm is prepared by punching using a puncher. The sample piece is placed in a well of a 24-well microplate for cell culture (Sumitomo Bakelite Co., Ltd.) such that the blood-contacting surface faces upward, and a metallic pipe-shaped weight with a wall thickness of 3 mm is loaded thereon. Platelet-rich plasma prepared separately is added to the well such that the number of platelets is about $10^8$ per well. The microplate is left to stand at 37° C. for 2 hours, and the sample is then removed therefrom and rinsed with PBS(−) (Nissui), followed by destroying platelets and measuring the activity of generated LDH according to the protocol described for LDH Cytotoxicity Detection kit (Takara Bio Inc.). Based on a calibration curve prepared separately, the number of adherent platelets is determined. As shown in Equation 1, the ratio of the number of platelets after contact with the sample piece to the number of platelets in the platelet-rich plasma before contact is determined, to provide the platelet adhesion rate.

Platelet adhesion rate (%)=(number of adherent platelets after the contact/number of platelets in platelet-rich plasma)×100    (1)

Cellular Adhesiveness

The artificial blood vessel is cut along the axial direction and a disk sample with a diameter of 12 mm is prepared by punching using a puncher. The sample piece is placed in a well of a 24-well microplate for cell culture (Sumitomo Bakelite Co., Ltd.), and a metallic pipe-shaped weight with a wall thickness of 3 mm is loaded thereon. Normal human umbilical vein endothelial cells (Takara Bio Inc.) suspended in DMEM medium supplemented with 10% FCS are added thereto such that $10^6$ cells are contained in the well. The microplate is left to stand at 37° C. for 12 hours, and the sample is then removed therefrom and rinsed with PBS(−) (Nissui), followed by detaching the cells by enzyme treatment and measuring the number of detached cells using an MTT Assay Kit (Funakoshi Corporation). As shown in Equation 2, the ratio of the number of adherent cells to the number of cells plated on the sample is determined, to provide the cell adhesion rate.

$$\text{Cell adhesion rate (\%)} = (\text{number of adherent cells}/\text{number of cells plated}) \times 100 \quad (2)$$

Thrombus Adhesion in Blood Circulation

The artificial blood vessel was cut into a length of 4 cm, and connected to a polyvinyl chloride tube having the same inner diameter as the artificial blood vessel, and a length of 32 cm. Into the tube, 4.5 mL of human fresh blood supplemented with heparin at a final concentration of 0.5 IU/mL was introduced and both ends were immediately sealed to form a loop. The prepared loop was fixed on a frame attached to a rotor operated at a rotation speed of 14 rpm in a thermo-hygrostat drier whose temperature was preliminarily adjusted to 37° C., and rotated for 120 minutes. The loop is then taken out, and the polyvinyl chloride tube is cut to remove blood, followed by rinsing with PBS(−) (Nissui). Thereafter, the presence or absence of thrombi formed in the artificial blood vessel is quantified. The test is carried out with N=3. The same test is carried out using, as a negative control, PBS(−) instead of the human fresh blood. The dry weight of the artificial blood vessel with a length of 4 cm is measured before the test and after the removal of blood and rinsing, and the difference between these measured values is regarded as the thrombus weight, and its mean and standard deviation are calculated. When the mean for the sample is not less than (mean+3×standard deviation) for the negative control, the result is evaluated as "+" and, when the mean for the sample is less than this value, the result is evaluated as "−". When leakage of blood is found through the artificial blood vessel during the circulation, the result is evaluated as "leakage" irrespective of the amount of blood leaked, and the test is stopped.

EXAMPLES

Examples of the artificial blood vessel are concretely described below in detail.

Examples

A tubular fabric was prepared as a plain-weave tissue using polyethylene terephthalate of 55 Dtex-48 f as a warp and polymer array fiber of 245 Dtex-40 f as a weft. The polymer array fiber used therefor was composed of 20 parts of polystyrene as sea-component and 80 parts of polyethylene terephthalate as island-component, and the number of islands was 36/f. This tube was sufficiently treated with an aqueous sodium hydroxide solution at 80° C., and immersed in toluene. Subsequently, the fabric was subjected to raising by using a raising machine, and then to water-jet punching.

The tubular fabric after the above-described treatments was then treated with 0.5% aqueous sodium hydroxide solution and then subjected to oxidation treatment with 5% potassium permanganate. Then polyethyleneimine (molecular weight 600, Wako Pure Chemical Industries, Ltd.) was added in the presence of 0.1% 1-(3-dimethylaminopropyl)-3-ethyl carbodiimide to react the fibers in the tubular fabric with polyethyleneimine. The polyethyleneimine immobilized on the surface of the fibers was converted to quaternary ammonium in 1% solution of ethyl bromide, butyl bromide, hexyl bromide, octyl bromide or decyl bromide in methanol at 50° C. Finally, the fabric was immersed in 0.8% aqueous heparin sodium (Wako Pure Chemical Industries, Ltd.) solution at 70° C., to provide an antithrombotic tubular fabric to be used as an artificial blood vessel.

Table 1 shows the performance evaluation results of each antithrombotic tubular fabric obtained by measurement of the water permeability, the residual heparin activity on the fiber surface after washing, the amount of cation on the fiber surface, the platelet adhesion rate, the cell adhesion rate, and thrombus adhesion.

The antithrombotic tubular fabric to which the quaternary ammonium group-containing polymer having C2 alkyl groups was covalently bound was designated as Sample 1, the antithrombotic tubular fabric to which the quaternary ammonium group-containing polymer having C4 alkyl groups was covalently bound was designated as Sample 2, the antithrombotic tubular fabric to which the quaternary ammonium group-containing polymer having C6 alkyl groups was covalently bound was designated as Sample 3, the antithrombotic tubular fabric to which the quaternary ammonium group-containing polymer having C8 alkyl groups was covalently bound was designated as Sample 4, and the antithrombotic tubular fabric to which the quaternary ammonium group-containing polymer having C10 alkyl groups was covalently bound was designated as Sample 5.

Example 2

The tubular fabrics prepared in Example 1 were immersed in aqueous solutions of polyethyleneimine (PEI), polyallylamine (PAA) and polydiallyldimethylammonium chloride (PDDA), respectively, and irradiated with γ-ray at 5 kGy at Koga Isotope under the condition of being immersed in the solution. The resulting fabrics were washed with Triton-X100 and water to obtain antithrombotic tubular fabrics. The tubular fabrics on which polyethyleneimine or polyallylamine was immobilized was subjected to the conversion to quaternary ammonium in the same manner as in Example 1 using ethyl bromide. To the tubular fabrics on which polyethyleneimine converted to quaternary ammonium, polyallylamine converted to quaternary ammonium and polydiallyldimethylammonium, respectively, were immobilized, heparin was ionically bound by the same method as in Example 1 to obtain antithrombotic tubular fabrics.

The antithrombotic tubular fabric obtained by binding polyethyleneimine by irradiation with γ-ray, conversion to quaternary ammonium, and ionic binding of heparin was designated as Sample 6, the antithrombotic tubular fabric obtained by binding polyallylamine by irradiation with γ-ray, conversion to quaternary ammonium, and ionic binding of heparin was designated as Sample 7, and the antithrombotic tubular fabric obtained by binding polydiallyldimethylammonium by irradiation with γ-ray, conversion to quaternary ammonium, and ionic binding of heparin was designated as Sample 8.

Table 1 shows the performance evaluation results of each antithrombotic tubular fabric obtained by measurement of the water permeability, the residual heparin activity on the fiber surface after washing, the amount of cation on the fiber surface, the platelet adhesion rate, the cell adhesion rate, and thrombus adhesion.

Comparative Example 1

The tubular fabric on which polyethyleneimine was immobilized described in Example 1 was bound with heparin by the same method as in Example 1, and the resulting fabric was designated as Sample 9. The antithrombotic tubular fabric prepared by covalently binding a quaternary ammonium group-containing polymer having C12 alkyl groups obtained by conversion of polyethyleneimine to quaternary ammonium with dodecyl bromide, and ionically binding heparin by the same method as in Example 1 was designated as Sample 10.

Comparative Example 2

The tubular fabrics described in Example 2 on which polyethyleneimine and polyallylamine were immobilized, respectively, were ionically bound with heparin by the same method as described in Example 1. The antithrombotic tubular fabric prepared by binding polyethyleneimine by irradiation of γ-ray, and ionically binding heparin was designated as Sample 11, and antithrombotic tubular fabric prepared by binding polyallylamine by irradiation of γ-ray, and ionically binding heparin was designated as Sample 12.

Comparative Example 3

A tubular fabric was prepared as a high-density plain-weave tissue using polyethylene terephthalate of 55 Dtex-48 f as a warp and polymer array fiber of 245 Dtex-40 f as a weft. The obtained tubular fabric was subjected to the same operations as in Example 1, and the obtained antithrombotic tubular fabric was designated as Sample 13.

Comparative Example 4

A tubular fabric was prepared using polyethylene terephthalate as both the warp and weft. The obtained tubular fabric was subjected to the same operations as in Example 1, and the obtained antithrombotic tubular fabric was designated as Sample 14.

Comparative Example 5

In 2 L of dimethylformamide, 120 g of polyvinyl chloride having a degree of polymerization of 550 was dissolved, and 704 g of sodium diethyldithiocarbamate was added. The obtained solution was allowed to react at 50° C. for 3 hours, reprecipitated in methanol and dried to obtain a photografted activated polyvinyl chloride (hereinafter referred to as "DTC-polyvinyl chloride"). In 1250 mL of tetrahydrofuran, 80 g of this DTC-polyvinyl chloride was dissolved, and 200 g of methoxypolyethylene glycol methacrylate (the degree of polymerization of the polyethylene glycol moiety was 20 to 23) and 80 g of dimethylaminoethyl methacrylate were added. The resulting solution was irradiated with a 100 W high pressure mercury lamp (Ushio Inc. UM-102) at 30° C. for 9.5 hours to carry out photografting polymerization. Ten percent solution of the obtained polymer in tetrahydrofuran was coated on the tubular fabric described in Example 1. After drying the fabric under reduced pressure for a whole day and night, tubular fabric ethyl bromide was added and the resultant was allowed to react at 50° C. After washing, heparin was ionically bound by immersing the fabric in aqueous 1% heparin solution at 60° C. After the reaction, the obtained antithrombotic tubular fabric was designated as Sample 15. The thickness of the coating was 20 μm.

Table 1 shows the performance evaluation results of each of the antithrombotic tubular fabrics of the Comparative Examples obtained by measurement of the water permeability, the residual heparin activity on the fiber surface after washing, the amount of cation on the fiber surface, the platelet adhesion rate, the cell adhesion rate, and thrombus adhesion.

TABLE 1

| | Sample | | Polymer | Carbon number in alkyl group | Water permeability (mL/cm$^2$/min) | Residual heparin activity on fiber surface after washing (mIU/cm$^2$) | Amount of cation on fiber surface (μg/cm$^2$) | Platelet adhesion rate (%) | Cell adhesion rate (%) | thrombus adhesion in loop test |
|---|---|---|---|---|---|---|---|---|---|---|
| Example 1 | 1 | PET fiber Ultrafine fiber | PEI | 2 | 2230 | 80 | 3.2 | 1 | 91 | – |
| | 2 | PET fiber Ultrafine fiber | PEI | 4 | 1870 | 79 | 2.4 | 2 | 86 | – |
| | 3 | PET fiber Ultrafine fiber | PEI | 6 | 2910 | 62 | 2.3 | 1 | 88 | – |
| | 4 | PET fiber Ultrafine fiber | PEI | 8 | 2470 | 46 | 2 | 3 | 72 | – |
| | 5 | PET fiber Ultrafine fiber | PEI | 10 | 1990 | 21 | 1.9 | 2 | 74 | – |
| Example 2 | 6 | PET fiber Ultrafine fiber | PEI | 2 | 2630 | 71 | 2.8 | 7 | 88 | – |
| | 7 | PET fiber Ultrafine fiber | PAA | 2 | 2400 | 70 | 3.1 | 4 | 80 | – |
| | 8 | PET fiber Ultrafine fiber | PDDA | 2 | 2120 | 69 | 3.1 | 10 | 89 | – |
| Comparative Example 1 | 9 | PET fiber Ultrafine fiber | PEI | 0 | 2870 | 18 | 0.3 | 12 | 73 | + |
| | 10 | PET fiber Ultrafine fiber | PEI | 12 | 2350 | 10 | 2 | 14 | 65 | – |
| Comparative Example 2 | 11 | PET fiber Ultrafine fiber | PEI | 0 | 2590 | 16 | 0.6 | 10 | 78 | + |
| | 12 | PET fiber Ultrafine fiber | PAA | 0 | 2610 | 16 | 0.5 | 16 | 73 | + |
| Comparative Example 3 | 13 | PET fiber Ultrafine fiber | PEI | 2 | 70 | 75 | 3.5 | 31 | 80 | + |
| Comparative Example 4 | 14 | PET fiber | — | PEI | 2 | 4290 | 74 | 2.5 | 24 | 29 | Blood leakage |
| Comparative Example 5 | 15 | PET fiber Ultrafine fiber | Graft polymer | 2 | 0 | 12 | 2.1 | 18 | 23 | – |

As shown in Table 1, when a quaternary ammonium group-containing polymer was immobilized, the residual heparin activity on the fiber surface of the artificial blood vessel was high and no thrombus formation occurred during the circulation. On the other hand, when a polymer containing no quaternary ammonium group was immobilized, the residual heparin activity was low, and thrombus formation occurred. With Sample 14 having a too high water permeability, blood leakage occurred in the loop test. When a quaternary ammonium group-containing polymer is immobilized, the surface heparin activity is high and the effect to suppress thrombus formation is high. When the thickness of the coating is large as in Sample 15, the fiber tissue is covered and cell adhesion was decreased.

INDUSTRIAL APPLICABILITY

Our materials can be used as an artificial blood vessel with which both antithrombogenicity and cellular affinity can be achieved, which promotes intimal formation after indwelling and maintains antithrombogenicity during intimal formation and which can maintain its patency for a long time.

The invention claimed is:

1. An artificial blood vessel comprising a tubular fabric comprising a fiber layer containing an ultrafine fiber(s) and an ultrafine fiber layer inside of the fiber layer, the ultrafine fiber layer composed of an ultrafine fiber(s) having a fiber diameter(s) of not less than 10 nm and not more than 3 μm, wherein
   a quaternary ammonium group-containing polymer having alkyl groups each with a carbon number 10 or less covalently bound to said ultrafine fiber(s);
   heparin ionically bound to said quaternary ammonium group-containing polymer; and
   residual heparin activity after washing with physiological saline at 37° C. for 30 minutes is 20 mIU/cm$^2$ or more.

2. The artificial blood vessel according to claim 1, wherein an amount of cation bound to a surface of the fiber(s) is 1 μg/cm$^2$ or more.

3. The artificial blood vessel according to claim 1, whose water permeability at 120 mmHg is not less than 100 mL/cm$^2$/min and less than 4000 mL/cm$^2$/min.

4. The artificial blood vessel according to claim 1, wherein said fiber layer is composed of said ultrafine fiber(s) and a multifilament(s), the multifilament(s) having a total fineness of 1 to 60 decitex.

5. The artificial blood vessel according to claim 4, wherein the fineness of single yarns constituting said multifilament is 0.5 to 10.0 decitex.

6. The artificial blood vessel according to claim 1, having a platelet adhesion rate of less than 20%.

7. The artificial blood vessel according to claim 1, wherein said tubular fabric is composed of a polyester fiber(s).

8. The artificial blood vessel according to claim 1, wherein the inner diameter of said tubular fabric is not less than 1 mm and less than 10 mm.

9. The artificial blood vessel according to claim 2, whose water permeability at 120 mmHg is not less than 100 mL/cm$^2$/min and less than 4000 mL/cm$^2$/min.

10. The artificial blood vessel according to claim 2, wherein said fiber layer is composed of said ultrafine fiber(s) and a multifilament(s), the multifilament(s) having a total fineness of 1 to 60 decitex.

11. The artificial blood vessel according to claim 3, wherein said fiber layer is composed of said ultrafine fiber(s) and a multifilament(s), the multifilament(s) having a total fineness of 1 to 60 decitex.

12. The artificial blood vessel according to claim 2, having a platelet adhesion rate of less than 20%.

13. The artificial blood vessel according to claim 3, having a platelet adhesion rate of less than 20%.

14. The artificial blood vessel according to claim 4, having a platelet adhesion rate of less than 20%.

15. The artificial blood vessel according to claim 5, having a platelet adhesion rate of less than 20%.

* * * * *